United States Patent [19]

Glover et al.

[11] 4,224,032
[45] Sep. 23, 1980

[54] METHOD AND APPARATUS FOR CHEMICAL ANALYSIS

[75] Inventors: Clyde P. Glover, Pittsford; James E. Ferris, Rochester; Robert J. Meyer, Spencerport; Edward Muka, Rochester, all of N.Y.

[73] Assignee: Eastman Kodak Company, Rochester, N.Y.

[21] Appl. No.: 857,344

[22] Filed: Dec. 5, 1977

Related U.S. Application Data

[63] Continuation of Ser. No. 751,872, Dec. 17, 1976, abandoned.

[51] Int. Cl.² .................. G01N 33/16; G01N 1/14
[52] U.S. Cl. .................. 23/230 B; 422/64; 422/65; 435/809
[58] Field of Search .................. 23/230 R, 230 B; 422/64–66; 195/127; 424/3; 353/113; 119/35, 39, 43; 435/809

[56] References Cited

U.S. PATENT DOCUMENTS

| | | | |
|---|---|---|---|
| 2,797,149 | 6/1957 | Skeggs | 422/82 |
| 3,036,893 | 5/1962 | Natelson | 422/66 |
| 3,136,609 | 6/1964 | Ciagne | 23/267 |
| 3,526,480 | 9/1970 | Findl | 422/66 |
| 3,574,064 | 4/1971 | Binnings et al. | 422/65 |
| 3,728,227 | 4/1973 | Elson et al. | 195/127 |
| 3,762,879 | 10/1973 | Moran | 422/66 |
| 3,788,816 | 1/1974 | Rohrbaugh et al. | 23/253 R |
| 3,825,410 | 7/1974 | Bagshawe | 422/61 |
| 3,832,135 | 8/1974 | Drozpowski et al. | |
| 3,883,308 | 5/1975 | Matte | 23/253 X |
| 3,904,372 | 9/1975 | Lightner | 73/61.1 C |
| 3,926,514 | 12/1975 | Costanza et al. | 353/113 |

FOREIGN PATENT DOCUMENTS 848287 8/1970 Canada.

Primary Examiner—R. E. Serwin
Attorney, Agent, or Firm—D. D. Schaper

[57] ABSTRACT

A method and apparatus are disclosed for performing chemical analysis on selected fluids. The apparatus comprises a turntable which carries a plurality of cartridges containing test slides. A transfer mechanism is adapted to receive a slide from a selected cartridge, transport the slide to a metering device where a precise amount of fluid is deposited thereon, and then deliver the slide to a conveyor which moves the slide through an incubator. A radiometric reading of the slide is taken while it is in the incubator.

28 Claims, 14 Drawing Figures

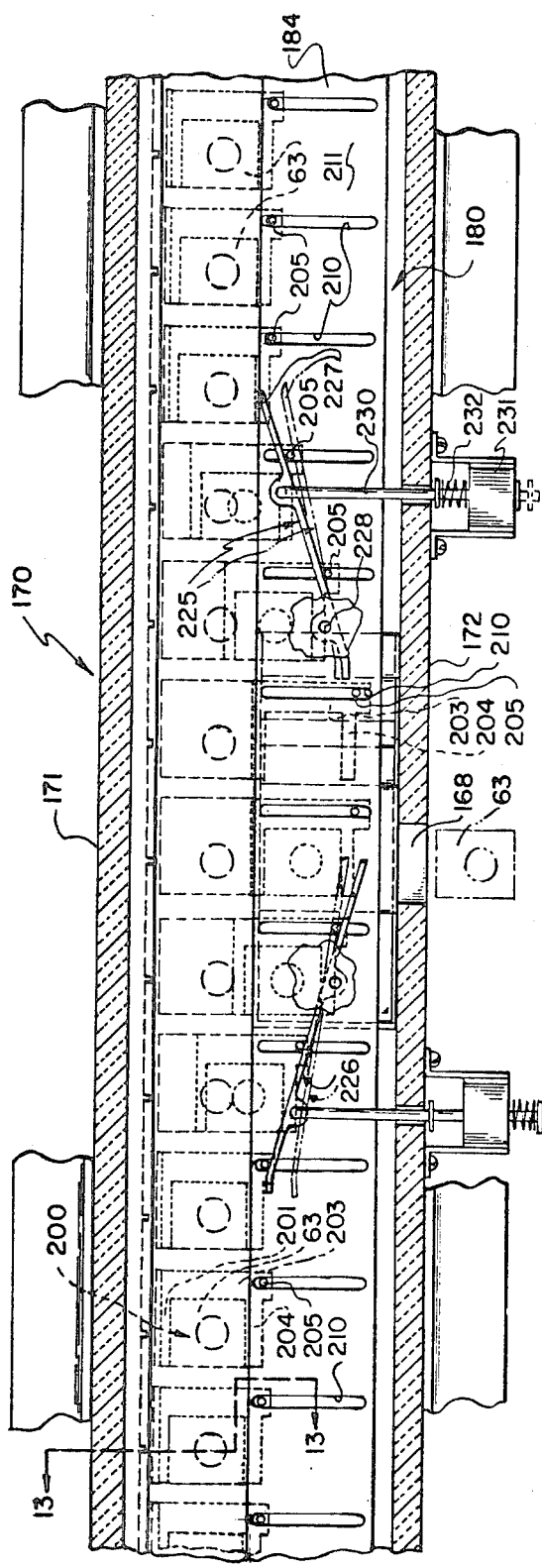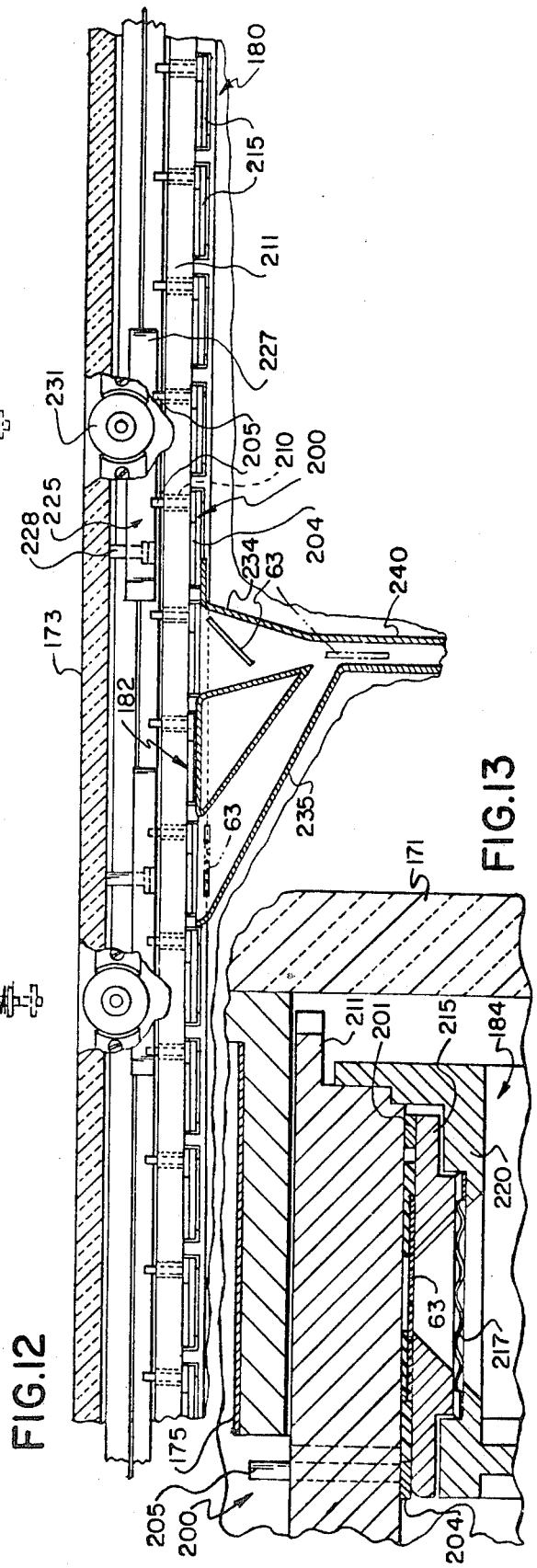
FIG.11
FIG.12
FIG.13

METHOD AND APPARATUS FOR CHEMICAL ANALYSIS

CROSS-REFERENCES TO RELATED APPLICATIONS

This application is a continuation of copending U.S. Patent Application Ser. No 751,872, filed Dec. 17, 1976, now abandoned.

Reference is made to commonly-assigned U.S. Pat. Applications: Ser. No. 644,014, entitled GAS-PRESSURE ACTIVATED DROP DISPENSER, filed in the name of Richard L. Columbus on Dec. 24, 1975, and now U.S. Pat. No. 4,041,995; U.S. Application Ser. No. 538,072, entitled INTEGRAL ANALYTICAL EMEMENT, filed in the name of Przybylowicz et al. on Jan. 2, 1975, and now U.S. Pat. No. 3,992,158; U.S. Application Ser. No. 751,869, entitled LOADING AND UNLOADING MECHANISM FOR CONTINUOUSLY ROTATING CONTAINER, filed in the name of R. Blakely et al. Dec. 17, 1976, and now U.S. Pat. No. 4,067,694; U.S. Application Ser. No. 751,873, entitled INCUBATOR AND RADIOMETRIC SCANNER, filed in the name of E. Muka et al. on Dec. 17, 1976, and now U.S. Pat. No. 4,119,381; and U.S. Application Ser. No. 751,912, entitled CHEMICAL ANALYZER, filed in the name of L. Nosco et al. on Dec. 2, 1977, and now U.S. Pat. No. 4,152,390

BACKGROUND OF THE INVENTION (1) Field of the Invention

This invention relates to the chemical analysis of substances, and more particularly, to a method and apparatus for the automatic analysis of biological fluids.

(2) State of the Prior Art

In recent years, a number of automated systems have been developed for carrying out quantitative chemical analyses of fluid samples. Most of the commercially-available systems utilize liquid reagents and require analyzer equipment having intricate solution handling and transport capabilities. One widely used system, shown in U.S. Pat. No. 2,797,149, employs a continuous-flow technique in which successive samples are separated from one another by immiscible fluid segments such as gas or air bubbles. Such a system is complex and expensive, requires skilled operators, and necessitates a considerable expenditure of time and effort in repetitive cleaning operations.

Another liquid analysis system is disclosed in U.S. Pat. No. 3,788,816, in which a turntable carries a plurality of receptacles containing samples to be analyzed and a pluraltiy of tube modules which are adapted to receive preset volumes of sample and reagent. Coaxially disposed relative to the turntable is a vertically movable rotary element comprising a probe tip which serves to dispense reagents and to transfer sample to a spectrophotometer.

U.S. Pat. No. 3,883,308, to Matte, discloses liquid analysis apparatus in which a plurality of sample containers are carried on a circular support, a plurality of reagent cups are supported on a second circular support, and an aspirator is provided for transferring fluid from a sample container to a selected reagent cup. The bottom portions of the reagent cups are transparent to facilitate a photometric reading through the container.

As an alternative to liquid analysis systems, various essentially-dry analytical elements have been adopted for automated test procedures. Although these elements offer substantial storage and handling conveniences, compared to "wet-chemistry," they have enjoyed only limited success and have been used primarily for qualitative and semi-quantitative test purposes. Apparatus for use with integral analytical elements in the form of continuous webs is shown in U.S. Pat. Nos. 3,036,893 and 3,526,480. Since the reagents are contained on the web in a predetermined sequence, the versatility of this apparatus is quite limited.

Automatic slide handling apparatus is known in clinical apparatus of the "wet-chemistry" type. In one such apparatus, shown in U.S. Pat. No. 3,574,064, glass slides are fed from a single supply station onto a turntable. Slides carried on the turntable are moved past a metering station, and then through wash and incubation stations spaced around the periphery of the turntable. Slides processed by the apparatus are ejected from the turntable into a slide receiver adjacent the slide supply station. There is no provision for automatic analysis of the processed slides, and they must be manually removed from the slide receiver for examination under a laboratory microscope.

U.S. Pat. No. 3,904,372, discloses apparatus for handling chromatographic plates in which plates are removed from a supply magazine by a pick-up arm, placed in position for spotting with an aliquot of fluid, and then transferred by the pick-up arm to a liquid development tank. The pick-up arm is pivotally mounted and utilizes a vacuum means to grip and hold the plates as they are transferred from the magazine to the development tank.

Slide handling mechanisms are also known in the photographic art. Representative of these mechanisms is the U.S. Pat. to Costanza et al., No. 3,926,514. This patent discloses a slide projector having a slide supply magazine which is supported above a turntable. Slides are fed from the magazine onto the turntable which moves the slides into a position for projection; after projection, the turntable moves the slide into a receiving chamber where the slides are collected for eventual restacking in the supply magazine. The Costanza et al. slides and apparatus are not indicated as being useful for performing radiometric analysis.

OBJECTS OF THE INVENTION

It is an object of the invention to provide apparatus and a process for analyzing biological fluids in which a fluid is metered onto discrete dry test slides which are analyzed after an appropriate period of incubation.

Another object of the invention is to provide apparatus for analyzing biological fluids which is adapted to process a plurality of slides in a preselected sequence.

Yet another object of the invention is to provide a chemical analyzer in which test slides are used to perform multiple analyses on a fluid sample selected from a plurality of fluid samples.

A further object of the invention is to provide slide transporting means for moving a selected slide from a supply point to a metering position and then to a conveyor means which is adapted to transport the slide through an incubator.

A still further object of the invention is to provide an analyzer having a plurality of channels for processing test slides.

Other objects and advantages will become apparent from the following Summary and Description of the Preferred Embodiments, when considered in light of the attached drawings.

SUMMARY OF THE INVENTION

This invention relates to a method and apparatus for the automatic analysis of biological fluids in which a fluid sample is metered onto a test slide which is analyzed after an appropriate period of the incubation.

In accordance with the invention, there is provided a slide supply means for receiving a stack of slides, each slide incorporating means to effect the analysis of a fluid sample. A sample supply means includes a plurality of fluid containers, and a metering means is adapted to deposit predetermined quantities of fluid onto slides successively moved into a metering position. A slide transporting means is adapted to remove a slide from a slide stack, move the slide to the metering position, and deliver the slide to a conveyor means cooperating with an incubator means. An analysis means senses a characteristic of the slide resulting from the fluid deposited thereon, after an appropriate period of incubation.

The invention is particularly suitable for use in performing analyses of blood sera in which the serum is dispensed onto a test slide of the type which is formed as a multilayer element containing the necessary reagents for reaction with components of the serum. However, this invention is not limited to use with just such test slides, nor is it limited to just the analysis of blood sera, as other fluids can be used with apparatus of the type disclosed.

BRIEF DESCRIPTION OF THE DRAWINGS

FIG. 11 is a fragmentary view of the incubator rotor, laid out in a straight line to show the slide loading mechanism;

FIG. 12 is an elevational view of the rotor, as viewed in FIG. 11.

FIG. 13 is an enlarged sectional view, taken along line 13—13 in FIG. 11; and

DESCRIPTION OF THE PREFERRED EMBODIMENTS

Figure 1:
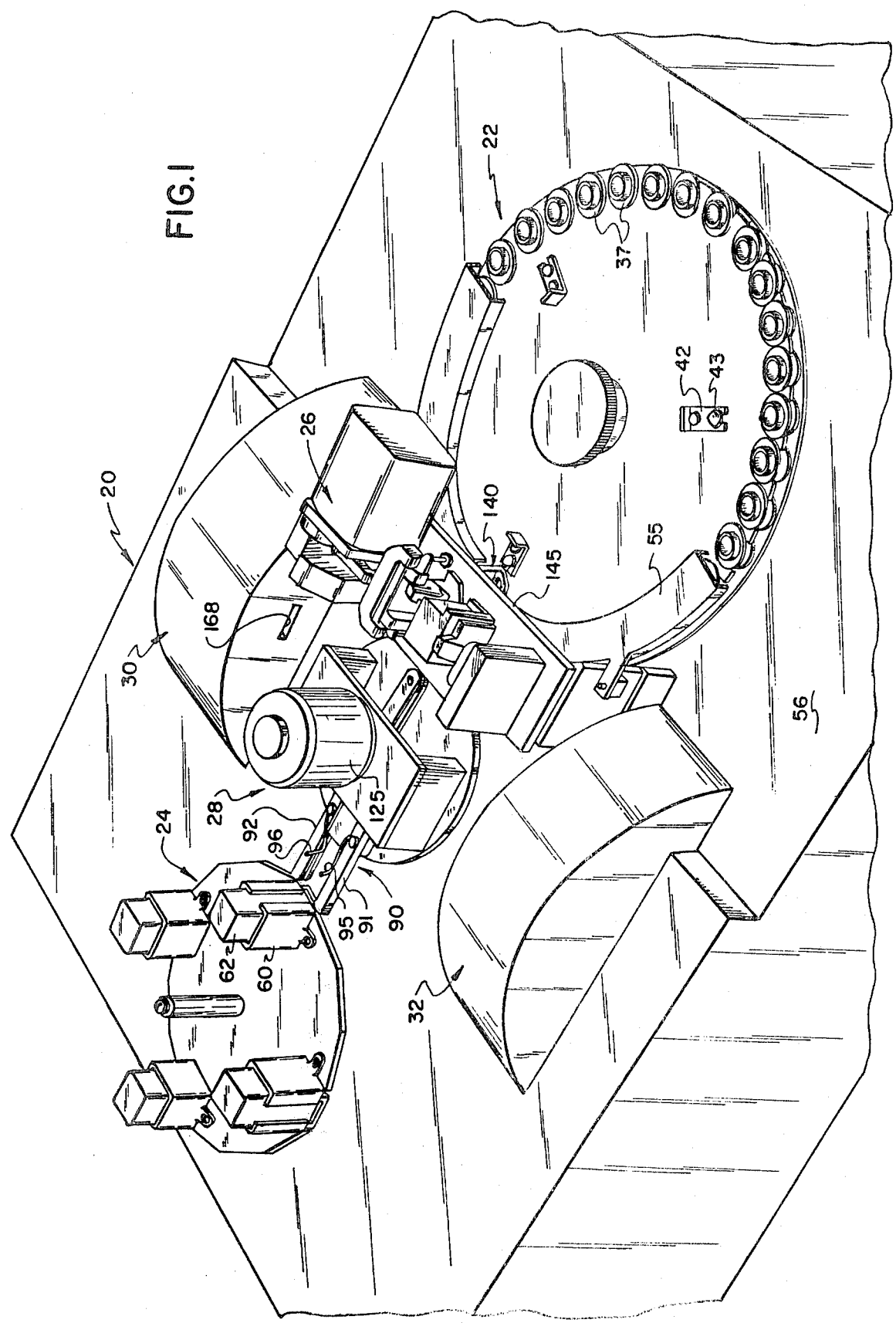
FIG. 1 is a perspective view of apparatus constructed in accordance with the invention.
Figure 9:
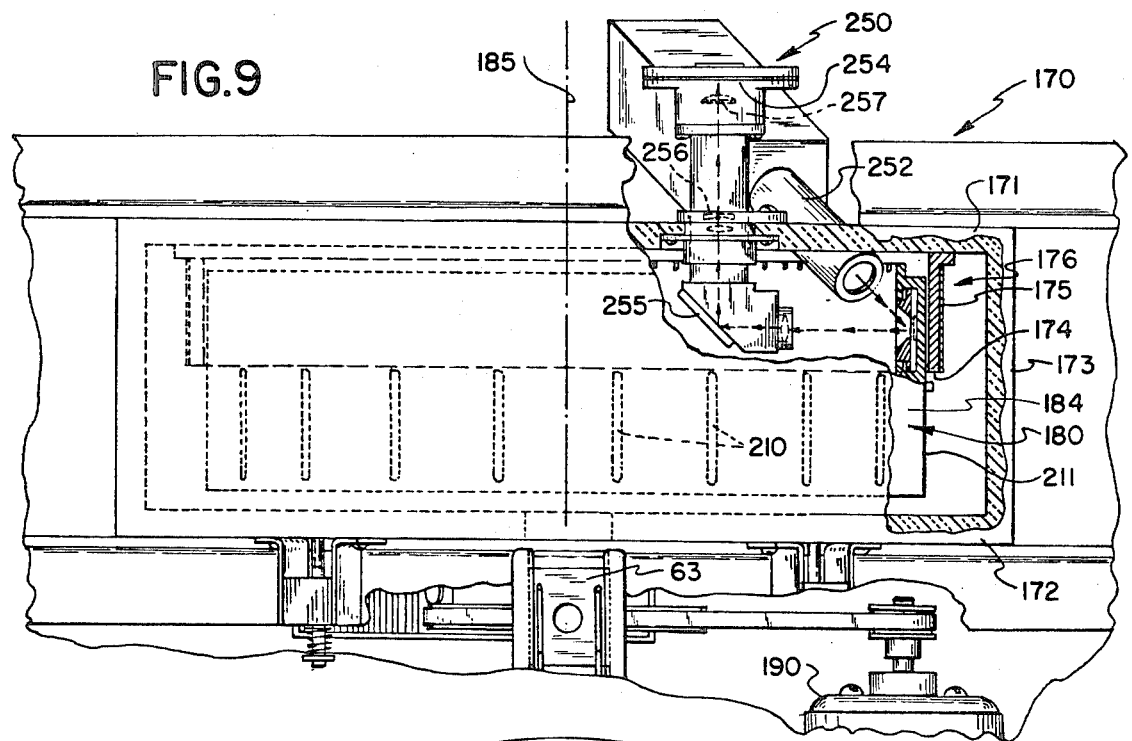
FIG. 9 is a top plan view of the incubator, with parts broken away to show the incubator rotor, the slide holding means in the rotor, and elements of the radiometer.
Figure 10:
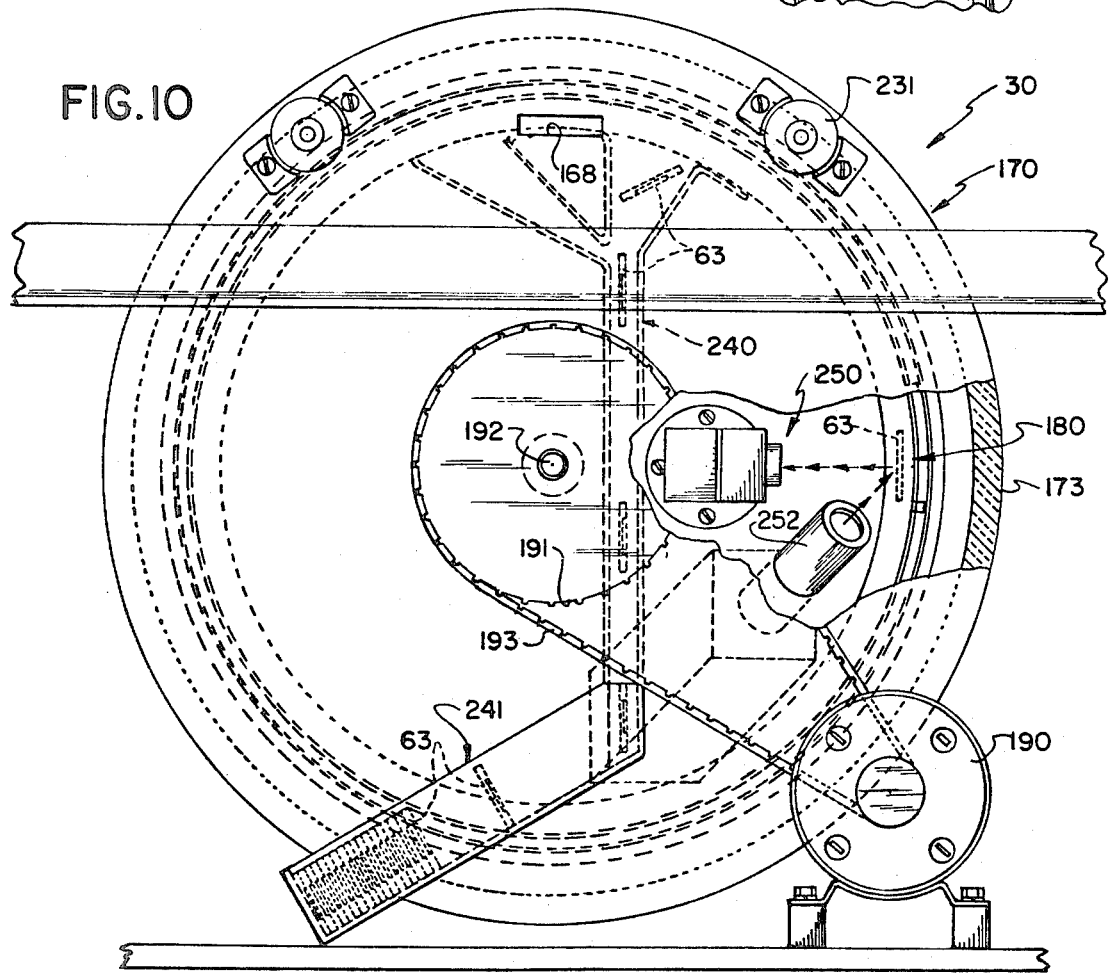
FIG. 10 is an elevational view of the incubator and the incubator drive means.

In accordance with one embodiment of the invention, there is shown in FIG. 1 a chemical analyzer 20 which comprises a sample tray 22, a reagent supply table 24, a metering device 26, a slide transfer mechanism 28, and incubators 30, 32. As will be discussed in more detail hereinafter, analyzer 20 is adapted to select a test slide from supply table 24, transport the slide to metering device 26 where a drop of biological fluid is placed thereon, and then deposit the slide in one of the incubators 30, 32. Analysis means (shown in FIG. 9) is adapted to take a radiometric reading of the slide after it has been in the incubator for an appropriate period of time.

Figure 2:
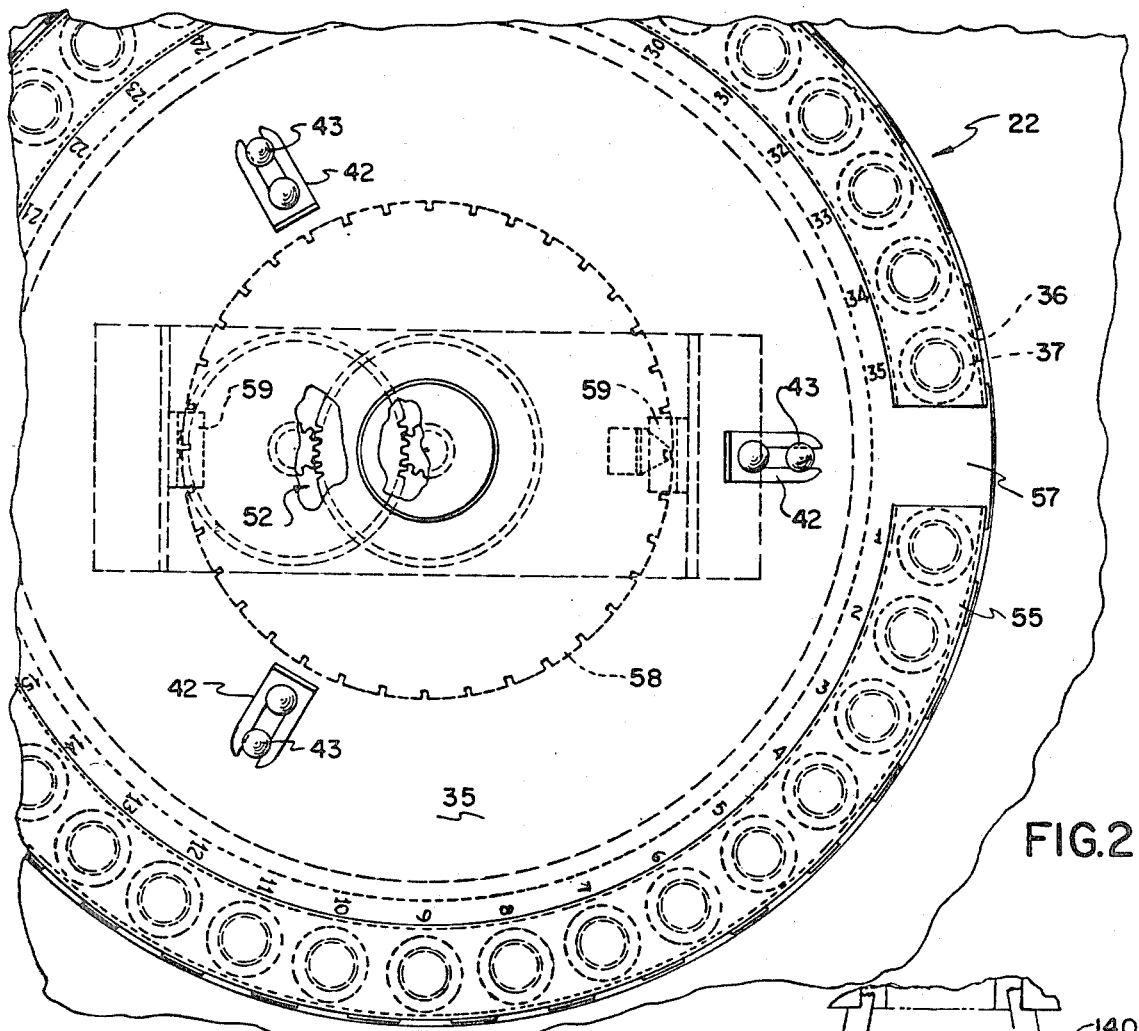
FIG. 2 is a fragmentary top plan view of the sample tray.
Figure 3:
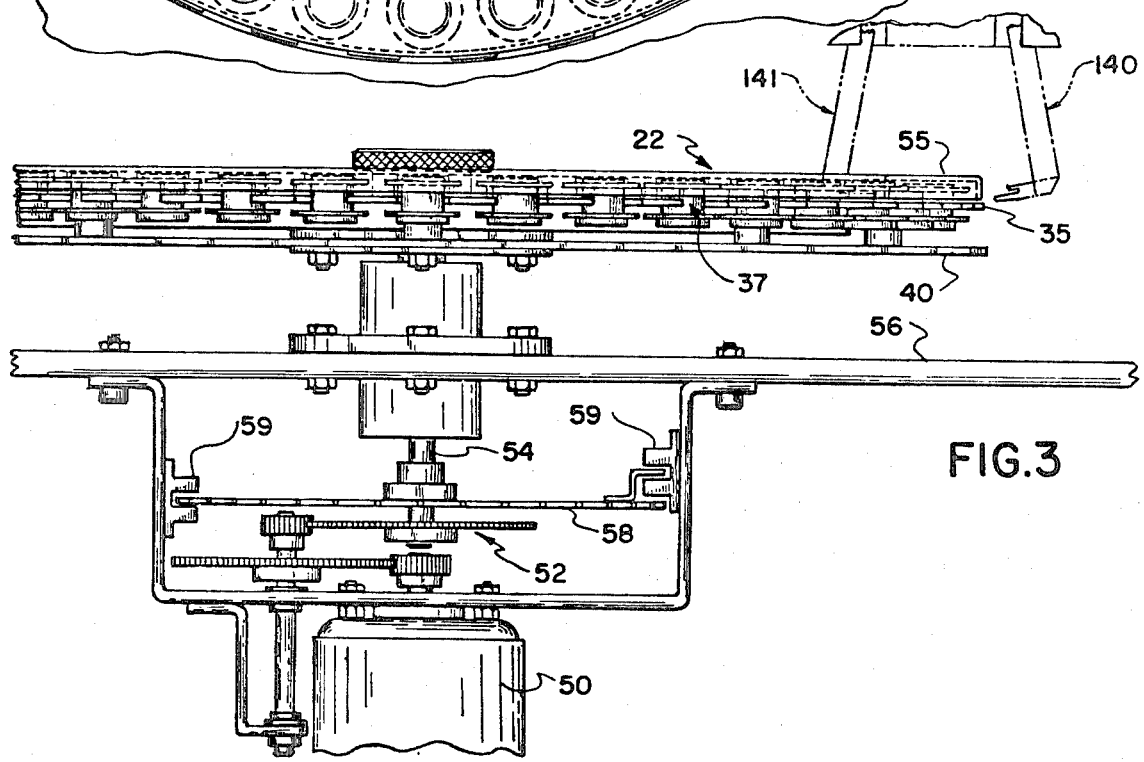
FIG. 3 is a fragmentary elevational view of the sample tray and the drive mechanism therefor.

Sample tray 22 is shown in detail in FIGS. 2 and 3. Tray 22 comprises a circular, generally flat top plate 35 which has a plurality of slots 36 formed around the periphery thereof; slots 36 are adapted to receive cups 37 which contain a biological fluid to be tested. Slots 36 are numbered 1–35 to provide a means for identifying the position of each of the samples to be analyzed. At the start of each test operation, tray 22 is mounted on the analyzer with the "home" position, designated 57, directly under metering device 26. As shown in FIGS. 2 and 3, a generally circular cover member 55 extends over the cups 37. Tray 22 is removably mounted on a carrier plate 40 by means of clips 42 which are movable in a radial direction to engage and disengage pins 43 on carrier plate 40. Sample tray 22 is rotated by a stepping motor 50 which transmits power through reduction gearing 52 to a drive shaft 54 journaled in base plate 56 of the analyzer; drive shaft 54 is fixed to carrier plate 40. An encoder wheel 58, carried on shaft 54, cooperates with photocells 59 to provide a means of locating a particular position in the sample tray.

Figure 4:
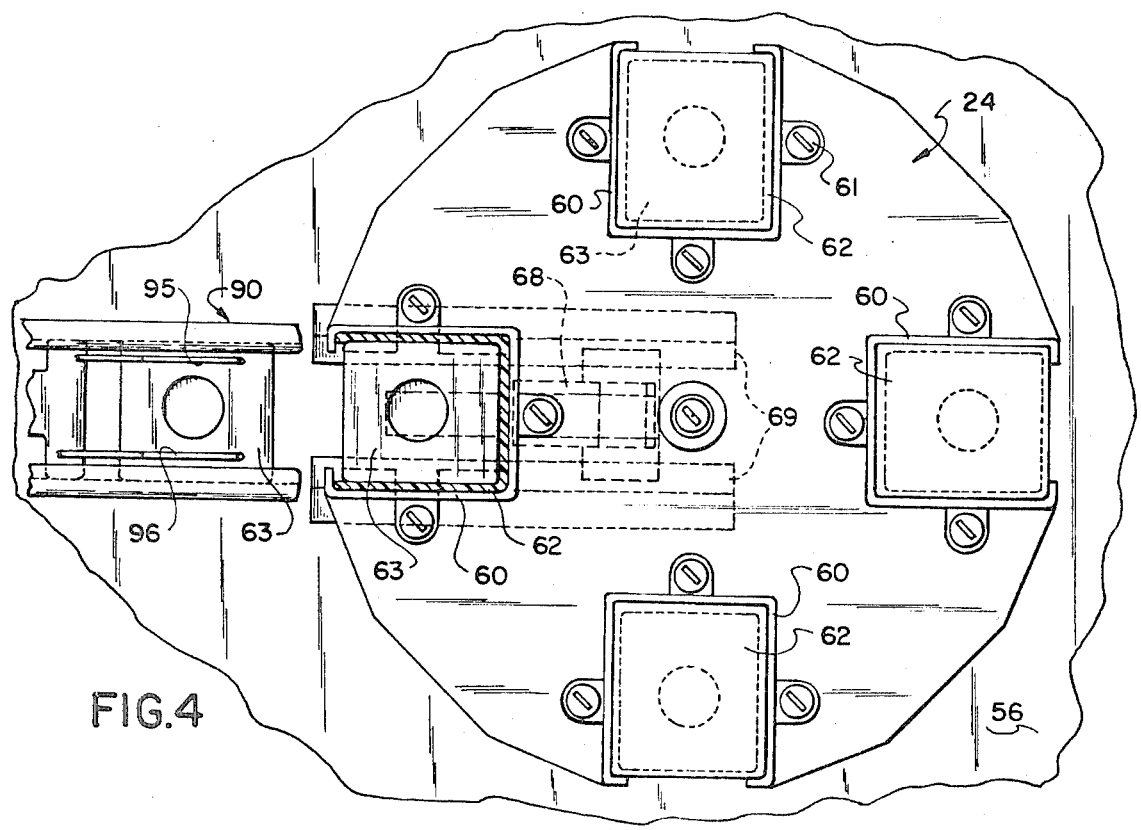
FIG. 4 is a top plan view of the slide supply table and showing a portion of the slide transfer mechanism.
Figure 5:
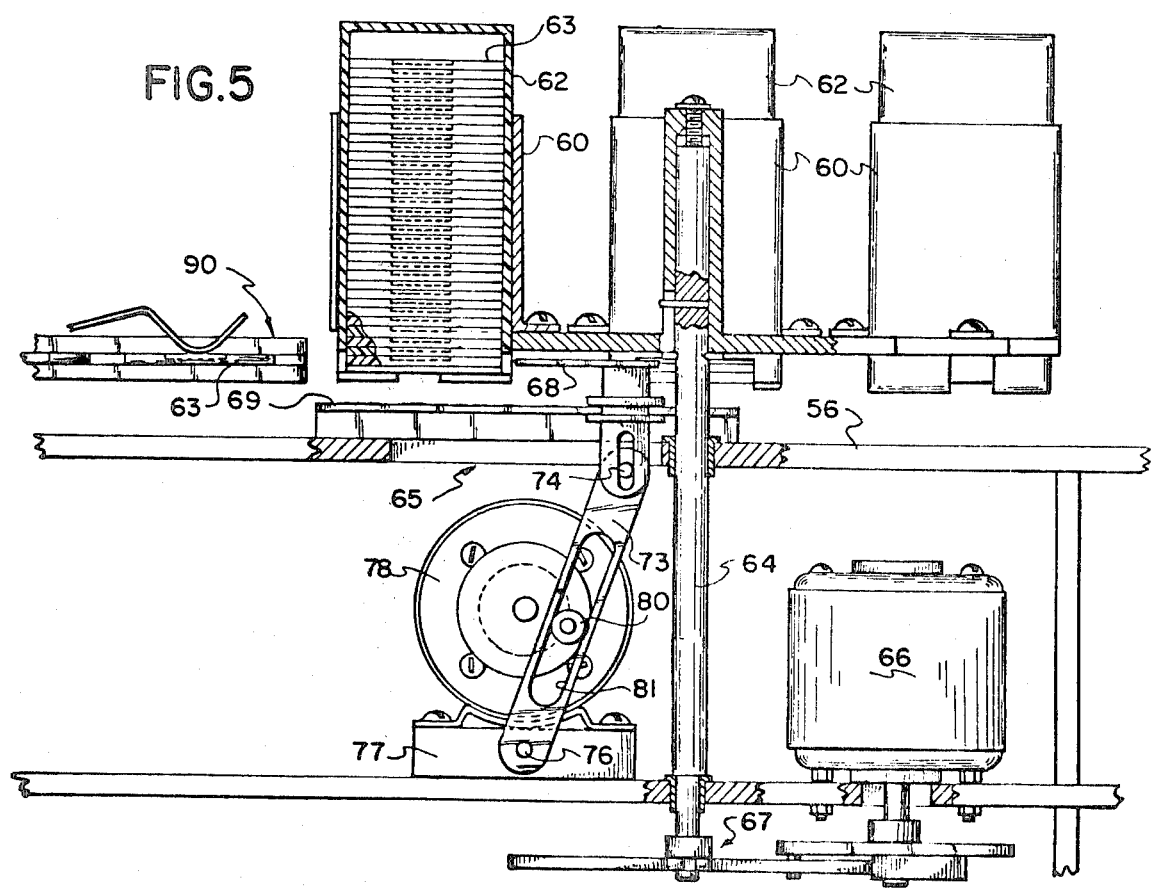
FIG. 5 is a vertical sectional view of the slide supply table, the slide ejector mechanism and a portion of the slide transfer mechanism.

Reagents for use in the analyzer are carried on reagent supply table 24, shown in FIGS. 4 and 5. Table 24 comprises a plurality of cartridge holders 60 which are secured to table 24 by screws 61. Mounted within holders 60 are cartridges 62 each of which contains a stack of test slides 63 suitable for use in the apparatus of this invention. Supply table 24 is rotatably mounted on a shaft 64 which is driven by motor 66 through a Geneva drive 67 to move a selected cartridge into the feed position adjacent arm 90.

A highly preferred form of slide for use with the subject invention is described in Belgian Pat. No. 801,402, granted on Jan. 2, 1974. The slides disclosed in the Belgian patent are formed as a multilayer element containing the necessary reagents for reaction with components of a biological fluid, such as blood serum, deposited thereon. Certain reactions colorimetrically produce a change in optical density which is sensed by a radiometer, the amount of light reflected from the element varying in accordance with the reaction and being indicative of the amount of a particular component present in the fluid.

The invention can also be used with other forms of slides, as for example, the slide disclosed in commonly-assigned U.S. Application, Ser. No. 687,725, entitled DEVICE AND METHOD FOR DETERMINING IONIC ACTIVITY OF COMPONENTS OF LIQUID DROPS, filed in the name of D. Hamblen et al. on May 19, 1976. This application describes a slide, or test element, of the type whic is used to potentiometrically designate the activity of ions in a liquid test solution by the use of electrodes.

Slides 63 are fed from cartridges 62 by an ejector mechanism 65 which includes a pusher element 68 slidably mounted on tracks 69 fixed to base plate 56. Pusher element 68 is driven by a crank 73 which is pinned to element 68 at 74 and is mounted for pivotal movement about a pin 76 fixed to motor mount 77. A motor 78 is adapted to rotate a roller 80 which rides in slot 81 in crank 73 and serves to oscillate crank 73 to push a slide out at the desired time.

Figure 6:
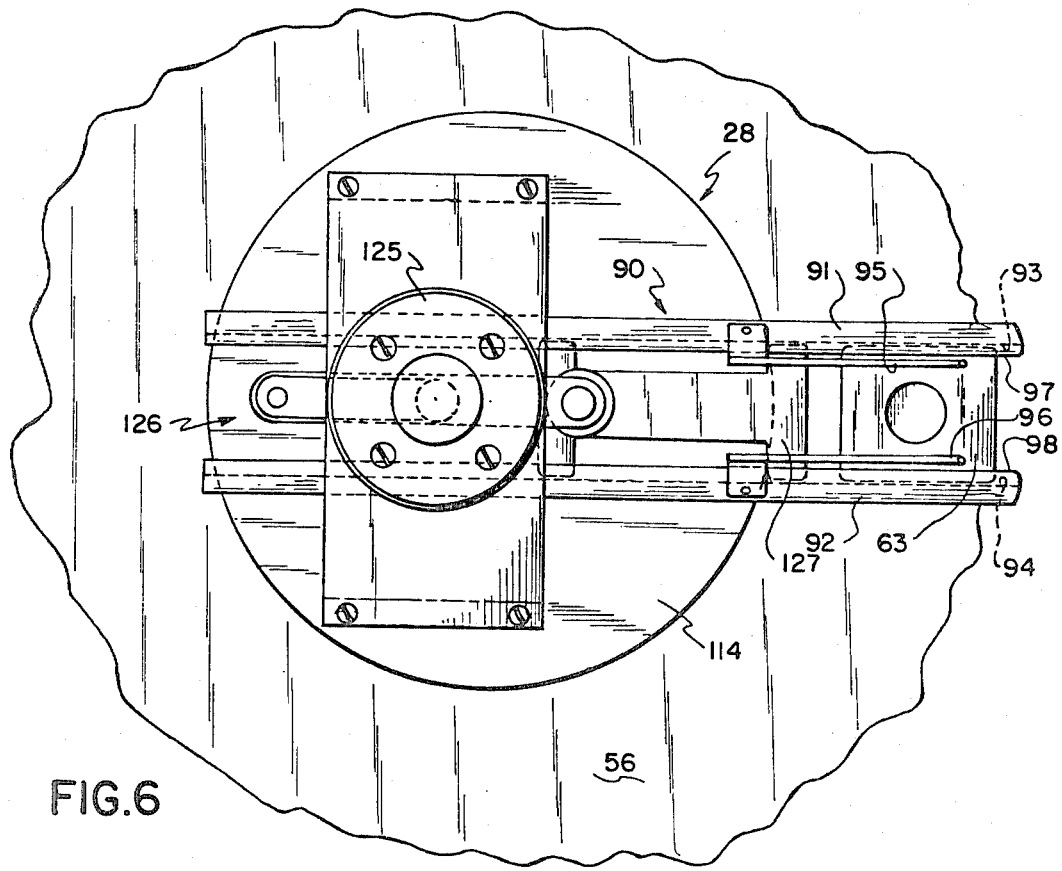
FIG. 6 is a top plan view of the slide transfer mechanism.
Figure 7:
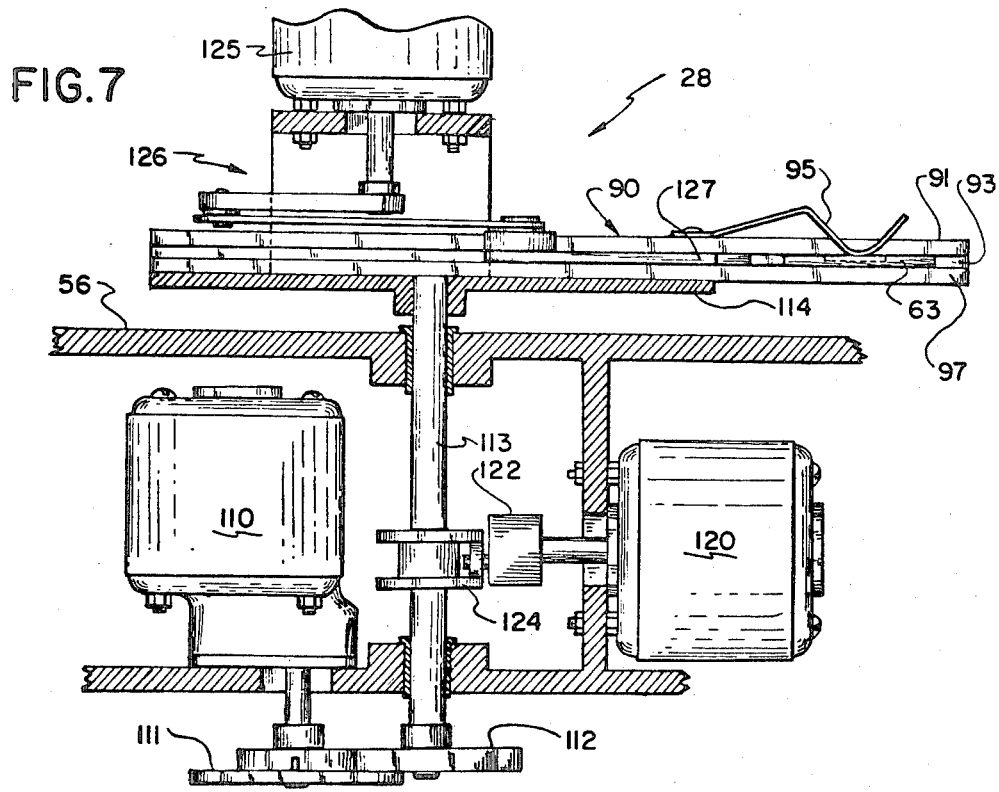
FIG. 7 is a fragmentary elevational view, partially sectioned, of the slide transfer mechanism and the drive means therefor.

Slide 63 is delivered by ejector mechanism 65 to arm 90 of the transfer mechanism 28 shown in FIGS. 6 and 7. Arm 90 comprises a pair of rails 91 and 92, rail 91 having a groove 93 formed on an inner face 97 and rail 92 having a groove 94 formed on its inner face 98; grooves 93 and 94 are adapted to receive slide 63 in a close-fitting relationship such that the slide will be accurately positioned relative to metering device 26. Springs 95 and 96 serve as a gripping means to hold the slide in arm 90. A motor 110 acts through gear 111 which drives Geneva gear 112 on drive shaft 113 to intermittently rotate a plate 114 which carries arm 90 thereon. A motor 120, connected to an eccentric 122 which is coupled to a collar 124 on shaft 113, is adapted to raise and lower table 114 and the arm 90 during the metering operation, described below.

Figure 8:
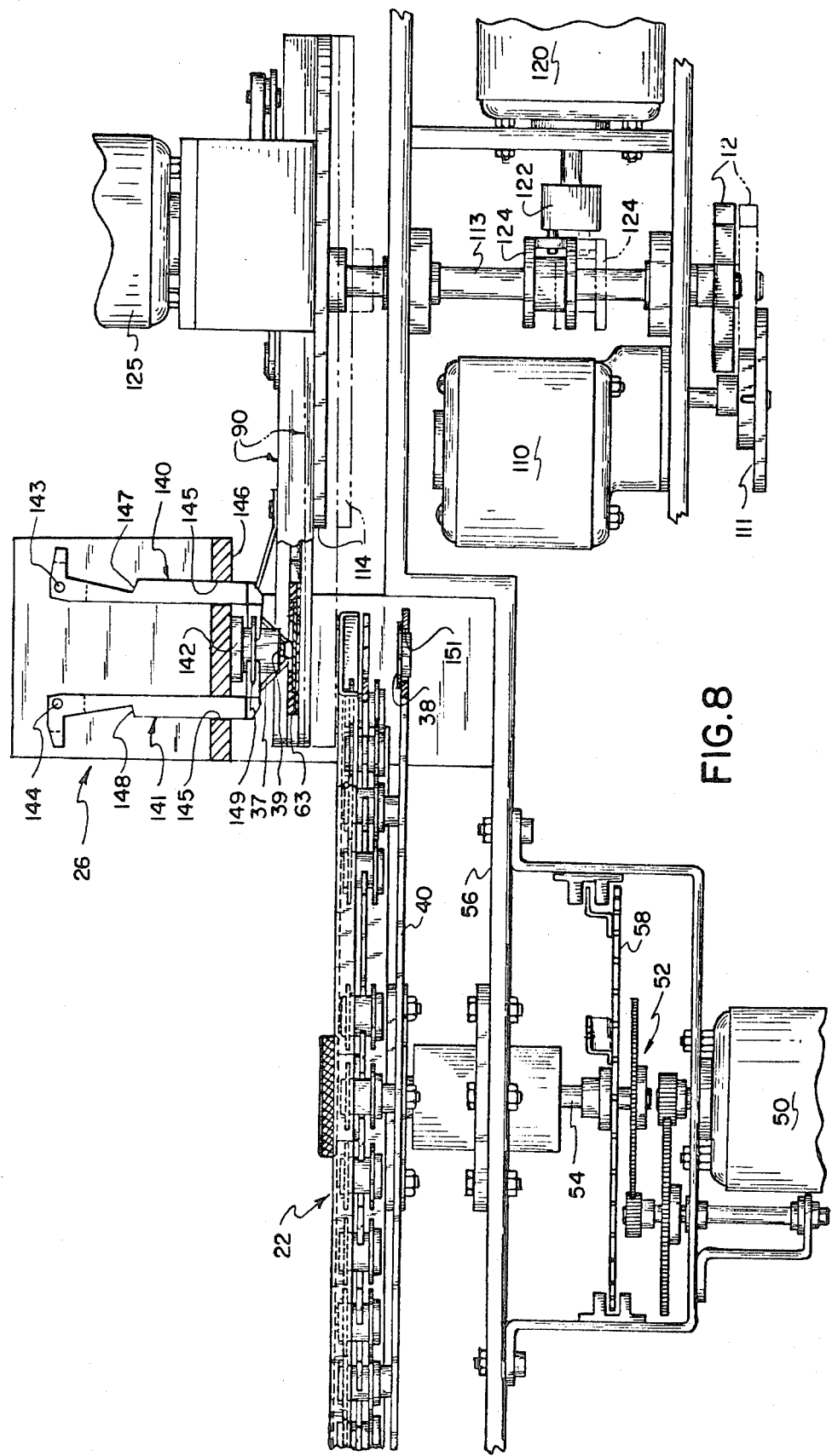
FIG. 8 is a fragmentary elevational view of the sample tray, metering device, and the slide transfer mechanism which is shown in the elevated position.

Movement of a slide 63 from the supply table to a metering position is accomplished by rotating arm 90 through 180°. Prior to moving the slide into the metering position, however, a cup 37 from sample tray 22 must be brought into engagement with metering device 26. As shown in FIG. 8, a pair of jaws 140, 141 are provided to lift cup 37 into engagement with a metering head 142. Jaws 140, 141, are pivotally mounted respectively at 143, 144, and the jaws are biased away from each other by a spring means, not shown. As the jaws are moved toward the sample tray 22 by a power means of a conventional type, not shown, the jaws will move in a generally straight line through openings 145 in plate 146 until notched portions 147, 148, are extended through openings 145; at this point the jaws are biased to the open position, shown in phantom in FIG. 3. On the return stroke, jaws 140, 141, will be cammed inwardly to engage a flange 149 on cup 37 and lift the cup into engagement whith head 142. After each metering operation, jaws 140, 141 are lowered to return the cup to the sample tray 22; the jaws remain in the position shown in FIG. 3 until a new sample cup 37 is advanced into the metering position. As cup 37 is moved upwardly by jaws 140, 141, a cup cap 38 is engaged by plate 35 which results in the cap being pulled off to expose a metering tip 39 on the cup. Caps 38 drop into holes 151 in plate 40. (See FIG. 8.)

When cup 37 is in position on metering head 142 and slide 63 is located under the cup, a pendant drop is formed on the metering tip 39 of the cup 37. A metering device, such as that disclosed in U.S. Application Ser. No. 644,014, and assigned to the assignee of the subject invention, is one form of metering apparatus and cup which is suitable for operation with this invention. The disclosure of U.S. Ser. No. 644,014 is incorporated herein by reference. As noted in Ser. No. 644,014 a pendant drop can be formed by pressurizing the air above the fluid in cup 37. To "touch-off" the pendant drop onto test slide 63, motor 120 is actuated to elevate table 114 and arm 90 of the transfer mechanism 28. (The elevated position is shown in solid lines in FIG. 8.) After the drop has been deposited on slide 63, motor 120 moves table 114, arm 90, and slide 63 to a lowered position (shown in phantom in FIG. 8); then motor 110 is actuated to rotate the table 90° to a position where the slide can be delivered to one of the incubators.

When arm 90 is positioned adjacent one of the incubators 30, 32, motor 125, acting through a crank mechanism 126, moves a pusher member 127 along grooves 93, 94, to push slide 63 through a slot 168 in incubator housing 170. (See FIG. 11.)

An incubator of a suitable type is shown in FIGS. 9–13; incubator 32 preferably is generally similar to incubator 30, and thus, only incubator 30 will be described in detail. Incubator housing 170 is constructed from a good insulating material and comprises a pair of end walls 171, 172, joined by a cylindrical wall 173 to form a chamber 176 in which temperature is carefully controlled. Affixed to a ring 174 on wall 171 is a heating element 175 which may be of the type in which high resistance wires are embedded in silicone rubber. Located within chamber 176 in housing 170 is a conveyor 180 which is adapted to receive slides 63 on a loading station 182 (FIG. 12) and to advance the slides through the incubator housing. A loading mechanism for conveyor 180, as disclosed herein, is described and claimed in the aforesaid copending Application Ser. No. 751,869, entitled "Loading and Unloading Mechanism for Continuously Rotating Container."

Conveyor 180 comprises a rotor 184 which is mounted for rotation about an axis 185. Rotor 184 is continuously driven by means of a motor 190 which drives a gear 191 on rotor shaft 192 through a belt 193. Space around the periphery of rotor 184 are a plurality of slide holding members 200 which are adapted to capture a slide from loading station 182, move the slide to a sensing position spaced axially from the loading station, and move the slide to a discharge chute 240 after analysis of the slide has been completed. (See FIG. 11.) Each of the members 200 is generally C-shaped and comprises a pair of legs 201, 204, joined by a cross member 203. A pin 205 fixed to member 200 adjacent leg 204 is adapted to move axially within the confines of slots 210 formed in an outer ring 211 of rotor 184. As best shown in FIG. 13, the lower portion of member 200 slides on a pressure plate 215 which is biased against member 200 by a circular spring 217 seated in an inner ring 220 of rotor 184.

Slide holding members 200 are axially moved on rotor 184 by the action of cam means 225, 226, which are adapted to engage pins 205 on members 200. Cam means 225 comprises a blade 227 which is pivotally mounted at 228 and is movable between the solid-line position shown in FIG. 11 and the phantom line position shown in the same figure. Blade 227 is connected through linkage 230 to a solenoid 231 which, upon actuation, moves the blade into the solid-line position (FIG. 11); a return spring 232 biases the blade away from the solid-line position. Elements of cam means 226 are generally similar to, and cooperate together in the same manner as, those just described for cam means 225.

When rotor 184 is moving from right to left, as viewed in FIG. 11, and solenoid 231 has been actuated, pin 205 of the selected member 200 will be engaged by blade 227 and the member will be moved axially toward wall 172. If a slide 63 is held by the member 200, it will be discharged into duct 234 of the discharge chute 240 as member 200 passes thereover; the member 200 will then engage a new slide 63 on loading station 182 (FIG. 12) and will be moved into a sensing position by cam means 226. In the event a slide is not properly engaged by a member 200, the slide will be pushed by the member 200 into a second duct 235 of discharge chute 240. Slides passing through chute 240 are collected, for disposal, in a receptacle 241. (See FIG. 10.)

As each slide 63 enters incubator 30, it is moved from the loading station 182 to a sensing position adjacent wall 171. Scanning of the slides is achieved by an analysis means, or radiometer, 250 (FIG. 9) which contains an energizing source 252, for example an incandescent bulb of suitable radiation, and a sensor 254 for detecting light reflected from the slide and directed to the detector by a planar mirror 255 and lens 256, 257.

The provision of two channels for the analysis of test slides significantly increases the number and type of tests which can be performed by the disclosed analyzer. The multichannel capability is achieved through the use of two separate incubator and analysis means together with a slide transfer mechanism which can deposit slides in either of the incubators. One possible arrangement would be to use incubator 30 for glucose tests and incubator 32 for BUN tests. To perform both tests, slide transfer mechanism 28 would receive a first test slide having the proper reagents for testing glucose, move the slide to the metering position where a drop of fluid would be dispensed onto the slide, and then deposit the slide in incubator 30; the same operation would be repeated for a BUN test slide which would be deposited in incubator 32. It would also be possible to perform rate analysis in one of the incubators and end-point analysis in another. Further, it will be apparent that one of the incubators could be used to process slides of the type disclosed in the aforesaid copending application, U.S. Ser. No. 687,725, in which case the slides would be analyzed by an electrometer, not shown.

Figure 14:
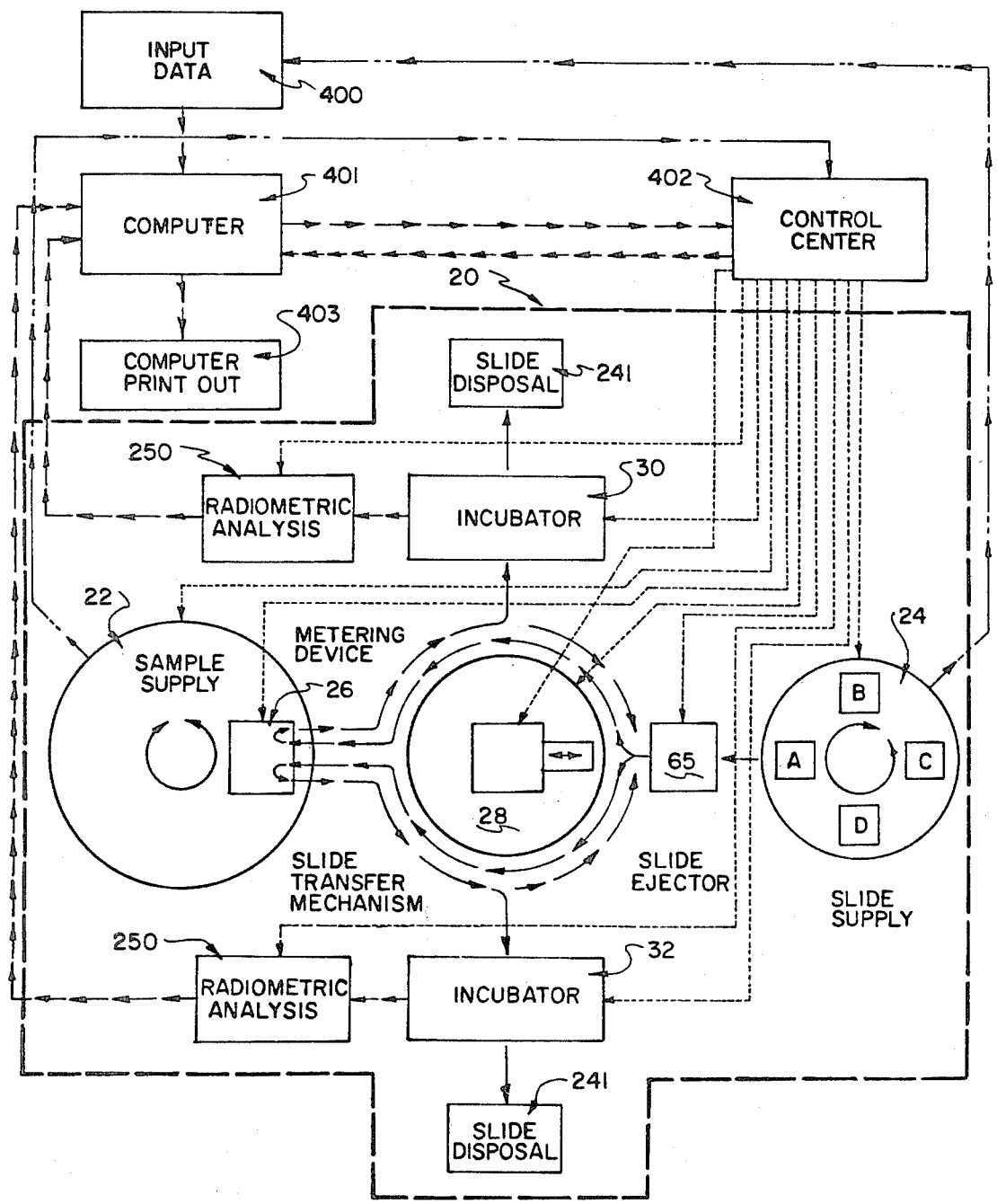
FIG. 14 is a schematic diagram of the apparatus of this invention and the controls therefor.

Operation of analyzer 20 can best be described by reference to FIG. 1 and to the schematic diagram shown in FIG. 14. Cups 37 containing fluid to be analyzed are loaded by the operator into sample tray 22, with a particular sample being located according to a numbered position on the tray. Tray 22 is placed on the machine with the home position 57 of the tray located directly under the metering device 26. Cartridges of test slides are loaded into supply table 24 such that slides for a particular test are in an identifiable position, e.g., slides measuring glucose in positions A and B (FIG. 14) and slides for measuring BUN in positions C and D. Input data 400, which includes calibration values, sample identification, and the desired tests for each fluid sample, is keyed into a computer, designated 401. Output signals from the computer are applied to control center 402 which provides input signals (dotted lines in FIG. 14) to the analyzer components to control their operation at the appropriate time in the machine cycle. Computer 400 may take any of the various forms known in the art which include commercially available programmable minicomputers and programmable microprocessors. The instructions and method of programming such computers is well known in the art, and thus, no further explanation is considered necessary here.

To start the analysis, slide ejector mechanism 65 loads a test slide 63 from cartridge A into transfer arm 90 of the slide transfer mechanism 28. As arm 90 is being moved toward the metering position, jaws 140, 141, pick up a sample cup 37 from tray 22 and raise it into engagement with the metering head 142. When the test slide 63 in arm 90 is located directly below metering tip 39 of the cup 37 in the metering device, a pendant drop is formed on the cup tip; arm 90 is then elevated to effect contact between the drop and the slide, causing the drop to be transferred to the slide. Arm 90 remains in the elevated position for an appropriate length of time and is then lowered and rotated to a position adjacent one of the incubators 30, 32, where the slide is delivered to the loading station 182 of the selected incubator. Slide 63 is moved into the incubator conveyor, as described above, and after an appropriate incubation time, a radiometric reading of the slide is taken. The results of the reading are transmitted to the computer which performs the necessary calculations, according to a stored program, to arrive at a concentration for a particular sample. This information, along with sample identification, is then transmitted to a display or printout device 403.

The invention has been defined in detail with reference to certain preferred embodiments thereof, but it will be understood that variations and modifications can be effected within the spirit and scope of the invention.

What is claimed is:

1. A method of performing chemical analysis of a fluid comprising the steps of:
    (a) removing a slide from a stack of slides, each of said slides including means to effect the analysis of a fluid sample;
    (b) transporting said slide to a metering position;
    (c) metering a predetermined quantity of fluid on said slide;
    (d) transporting said slide to incubator means, said incubator means having a plurality of conveyor means;
    (e) depositing said slide in a selected one of said conveyor means;
    (f) conveying said slide to a position to cooperate with an analysis means after an appropriate period of incubation; and
    (g) sensing a characteristic of said slide resulting from the fluid deposited thereon.

2. A method, as defined in claim 1, wherein said fluid is stored in a container and the fluid is metered from said container.

3. A method, as defined in claim 2, wherein said sensing of the slide is performed while said slide is in said conveyor means.

4. In an automatic chemical analyzer comprising sample supply means for receiving a plurality of containers of fluid sample, reagent supply means for receiving a stack of slides each of which contains a reagent, metering means adapted to dispense a predetermined quantity of fluid sample onto a slide, and incubator means, the improvement wherein:
    (a) conveyor means is provided in said incubator means, said conveyor means having a plurality of members for receiving slides bearing fluid sample and means for advancing the slides through said incubator means;
    (b) slide transporting means is provided for removing a slide from said stack, transporting said slide to a metering position where said quantity of fluid sample is deposited on the slide by said metering means, and delivering the slide to a selected one of said members; and
    (c) analysis means is operatively associated with said conveyor means.

5. An analyzer, as defined in claim 4, wherein said slide transporting means includes ejector means for removing a slide from said reagent supply means and transfer means adapted to receive a slide from said ejector means.

6. An analyzer, as defined in claim 5, wherein said transfer means includes a transfer arm having gripping means adapted to receive and hold a slide, said arm is mounted for rotation in either of two directions, and a pusher member is adapted to move a slide out of said gripping means.

7. An analyzer, as defined in claim 6, wherein said metering means is adapted to form a pendant drop, and said metering means and said transfer arm are movable relative to each other to deposit said drop on a slide in said arm.

8. An analyzer, as defined in claim 7, wherein said incubator devices have different operating characteristics whereby different analyses are carried out in the respective devices.

9. A chemical analyzer for measuring a characteristic of a fluid, said analyzer comprising in combination:
slide supply means for receiving at least one stack of slides, each slide including means to effect the analysis of a fluid;
sample supply means for receiving a plurality of containers of fluids to be analyzed;
metering means for depositing a predetermined quantity of fluid onto a slide supported in a metering position;
incubator means for providing a controlled environment for slides bearing said fluid, said incubator means having a loading station for receiving slides;
conveyor means operative in said incubator means, said conveyor means comprising a plurality of slide holding members each of which is adapted to receive and releasably hold a slide, said conveyor means further comprising means for advancing said slide holding members past said station;
analysis means operative after a slide has been in the incubator means a predetermined time for sensing a characteristic of said slide resulting from the fluid deposited thereon; and
slide transporting means for removing a slide from said stack, moving the slide to said metering position, and delivering the slide to a selected slide holding member in said conveyor means.

10. A chemical analyzer, as defined in claim 9, wherein said slide contains a reagent which is adapted to react with a component of said fluid to effect a change which can be radiometrically detected.

11. An automatic chemical analyzer, as defined in claim 9, wherein said slide is capable of potentiometrically designating the activity of ions in said fluid.

12. An analyzer, as defined in claim 9, wherein said slide transporting means includes ejector means for removing a slide from said slide supply means and transfer means adapted to receive a slide from said ejector means.

13. An analyzer, as defined in claim 12, wherein said slide supply means includes a table mounted for rotation and adapted to receive and support a plurality of slide stacks, and said ejector means includes a pusher element adapted to move a slide from one of said stacks into gripping means on said transfer means.

14. An analyzer, as defined in claim 12, wherein said transfer means includes a rotatably mounted transfer arm for supporting a slide and a pusher member for moving the slide from the arm into said conveyor means.

15. An analyzer, as defined in claim 14, wherein said metering means is adapted to form a pendant drop, and said transfer arm and said metering means are movable relative to each other to deposit said drop on the slide supported by said arm.

16. An analyzer, as defined in claim 9, wherein said sample supply means includes a carrier adapted to receive said containers, and said carrier being adapted to successively position said containers adjacent said metering means.

17. An analyzer, as defined in claim 8, wherein said incubator means includes a housing, said conveyor means comprises a rotor in said housing, and said slide holding members are spaced around the periphery of the rotor.

18. An analyzer, as defined in claim 17, wherein said analysis means is at least partially located within said housing and is adapted to measure radiation reflected from a slide held in said rotor.

19. An analyzer, as defined in claim 9, wherein said incubator means includes a pair of housings, said conveyor means includes a conveyor in each of said housings, and said slide transporting means is adapted to selectively deliver a slide to either of said conveyors.

20. An analyzer, as defined in claim 9, wherein said slide transporting means comprises transfer means, and said transfer means and said slide supply means are rotatable in either of two directions.

21. An analyzer, as defined in claim 9, wherein each of said containers comprises a metering tip and a cap covering said tip, and means are provided for automatically removing said cap at the metering position.

22. An analyzer, as defined in claim 9, wherein said slide supply means comprises a supply table having a plurality of slide stacks, said sample supply means includes a rotatively mounted sample tray and said containers are spaced around the periphery thereof, and said slide transporting means comprises transfer means mounted for rotation relative to said table and said tray.

23. An analyzer, as defined in claim 9, wherein programmed means are provided for automatically controlling sequential operation of said means.

24. An analyzer for measuring a characteristic of a fluid sample wherein the sample is deposited on a test slide which is analyzed after an appropriate period of time under controlled conditions, said analyzer comprising:
slide supply means for receiving a plurality of stacks of slides, one of said stacks including slides to effect an analysis of a first type and another of said stacks including slides to effect an analysis of a second type;
sample supply means for receiving a plurality of discrete samples;
metering means adapted to deposit a predetermined quantity of fluid from a selected sample onto a slide in a metering position;
incubator means including a plurality of temperature controlled chambers and conveyor means for advancing slides within the chambers, on of said chambers being adapted to accept slides of said first type and another of said chambers being adapted to accept slides of the second type;
analysis means adapted to cooperate with each of said chambers, said analysis means being operative after a slide has been in a chamber for a predetermined time to sense a characteristic of the slide resulting from the fluid deposited thereon; and slide transport means for removing a slide from a stack, moving the slide to said metering position and delivering the slide to a selected one of said chambers.

25. An analyzer for measuring a characteristic of a fluid sample wherein a sample is deposited on a test slide which is analyzed after an appropriate period of incubation, said analyzer comprising:

sample supply means for receiving fluid samples to be analyzed;

slide supply means for receiving a plurality of types of test slides and for delivering a selected type of test slide to a feed position;

metering means for depositing a predetermined quantity of sample on a test slide;

incubator means including a plurality of separate devices arranged to operate on individual slides;

analysis means for sensing a characteristic of a slide resulting from the fluid sample deposited thereon, said analysis means being adapted to cooperate with each of said devices;

means for transporting a slide from said supply means to said metering means and from said metering means to a selected one of said devices; and means for controlling the operation of said previously recited means in a preselected sequence to provide for the continuous analysis of fluid samples.

26. An analyzer, as defined in claim 24, wherein; said slide transport means includes a transfer means mounted for rotation through a circular path, and said slide supply means, sample supply means, metering means, and incubator means are arranged at spaced locations along said path.

27. An analyzer, as defined in claim 24, wherein said slide transport means, said conveyor means, said sample supply means, and said slide supply means are mounted for rotation.

28. Slide transporting means for use in a chemical analyzer of the type in which a fluid is metered onto a test slide which is analyzed after an appropriate period of incubation, said analyzer having a plurality of elements arranged along and outside of a circular path, said elements comprising slide supply means, sample supply means, metering means, and incubator means, said slide transporting means comprising:

transfer means for receiving a slide from said slide supply means, moving the slide to said metering means, and delivering the slide to said incubator means, said transfer means being movable through said circular path; and control means for moving said transfer means in timed relation to said analyzer elements.

* * * * *

UNITED STATES PATENT OFFICE
CERTIFICATE OF CORRECTION

PATENT NO. : 4,224,032
DATED : Sep. 23, 1980
INVENTOR(S) : Clyde P. Glover, James E. Ferris, Robert J. Meyer, and Edward Muka It is certified that error appears in the above-identified patent and that said Letters Patent are hereby corrected as shown below:

Col. 1, line 20    after al. insert --on--

Col. 4, line 66    "whic" should read --which--

Col. 5, line 44    "whith" should read --with--

Col. 10, line 60    "on" should read --one--

Signed and Sealed this

Thirteenth Day of January 1981

[SEAL]

Attest:

SIDNEY A. DIAMOND

Attesting Officer    Commissioner of Patents and Trademark